(12) United States Patent
Joseph et al.

(10) Patent No.: US 11,986,571 B2
(45) Date of Patent: May 21, 2024

(54) RADIOPAQUE POLYMERIC LIQUID EMBOLIC SYSTEM

(71) Applicant: SREE CHITRA TIRUNAL INSTITUTE FOR MEDICAL SCIENCES AND TECHNOLOGY, Thiruvananthapuram (IN)

(72) Inventors: Roy Joseph, Thiruvananthapuram (IN); Jayadevan Enakshy Rajan, Thiruvananthapuram (IN); Gopika Valsalakumari Gopan, Thiruvananthapuram (IN)

(73) Assignee: SREE CHITRA TIRUNAL INSTITUTE FOR MEDICAL SCIENCES AND TECHNOLOGY, Kerala Thiravanthapuram (IN)

( * ) Notice: Subject to any disclaimer, the term of this patent is extended or adjusted under 35 U.S.C. 154(b) by 623 days.

(21) Appl. No.: 17/291,075

(22) PCT Filed: Apr. 1, 2020

(86) PCT No.: PCT/IN2020/050317
§ 371 (c)(1),
(2) Date: May 4, 2021

(87) PCT Pub. No.: WO2020/202210
PCT Pub. Date: Oct. 8, 2020

(65) Prior Publication Data
US 2021/0402051 A1 Dec. 30, 2021

(30) Foreign Application Priority Data
Apr. 3, 2019 (IN) .............................. 201941013381

(51) Int. Cl.
*A61L 24/00* (2006.01)
*A61L 24/06* (2006.01)

(52) U.S. Cl.
CPC ......... *A61L 24/001* (2013.01); *A61L 24/0015* (2013.01); *A61L 24/06* (2013.01); *A61L 2300/106* (2013.01); *A61L 2300/418* (2013.01); *A61L 2430/36* (2013.01)

(58) Field of Classification Search
None
See application file for complete search history.

(56) References Cited

U.S. PATENT DOCUMENTS

| 6,017,977 A | 1/2000 | Evans et al. |
| 2013/0085238 A1* | 4/2013 | Bolikal ............... C08G 63/672 528/206 |

FOREIGN PATENT DOCUMENTS

| EP | 0938325 B1 | 6/2003 |
| EP | 2365009 A1 | 9/2011 |
| EP | 2832380 B1 | 11/2016 |

OTHER PUBLICATIONS

International Search Report and Written Opinion for International Application No. PCT/IN2020/050317, dated Oct. 8, 2020.

* cited by examiner

*Primary Examiner* — Brian Gulledge
(74) *Attorney, Agent, or Firm* — Dinsmore & Shohl LLP

(57) ABSTRACT

The invention relates to radiopaque liquid embolic composition comprising tetra iodo compound, 4,4-bis (4-hydroxy-3,5 diiodo phenyl) valeric acid (IBHV) of Formula I, covalently linked to ethylene vinyl alcohol copolymer (EVOH) and dissolved in a water miscible organic liquid.

9 Claims, 5 Drawing Sheets

Where RCOOH =

RADIOPAQUE POLYMERIC LIQUID EMBOLIC SYSTEM

FIELD OF INVENTION

Figure 1:
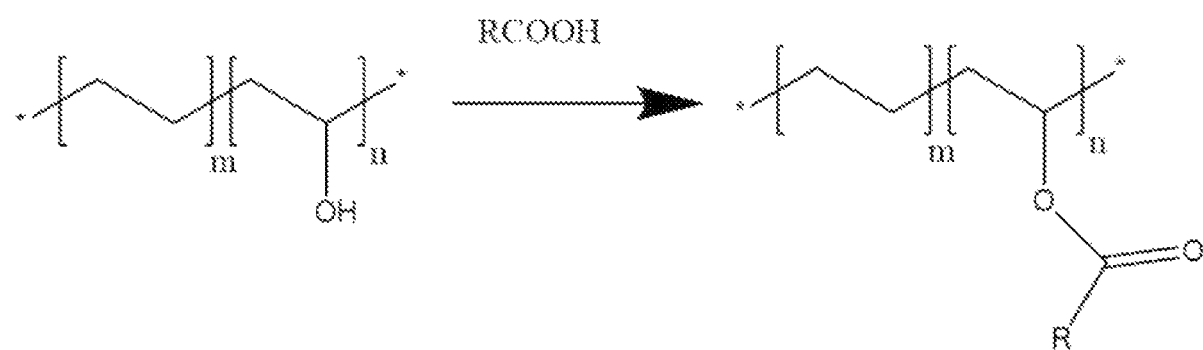
Figure 1:
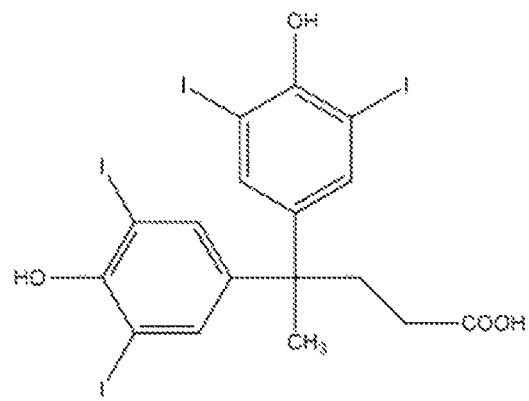

This invention relates to a radiopaque liquid embolic composition.

This invention further relates to a radiopaque liquid embolic composition consisting of a polymer covalently linked with a tetraiodo compound, 4,4-bis (4-hydroxy-3,5 diiodo phenyl) valeric acid, which precipitates upon contact with biological fluid and block the blood vessel. The modified polymer is biostable, inherently radiopaque, non-adhesive, non-toxic, non-hemolytic and suitable for medical applications. The polymer present in the liquid embolic composition is a chemically modified ethylene vinyl alcohol copolymer dissolved in solvents such as dimethyl sulfoxide or N-methyl pyrrolidone.

BACKGROUND OF THE INVENTION

Polymeric materials are used in several medical applications. One of the examples is therapeutic embolization which involves the selective blockage of the blood vessels or diseased vascular structures. The embolization of blood vessels is conducted as an alternative to surgical interventions for a variety of purposes including the treatment of tumors, lesions such as aneurysms, arteriovenous malformation, arteriovenous fistula, etc. Embolization is achieved through a catheter which helps the placement of embolic agent in the desired site. The first agent used for embolization therapy was autologous blood clot. This was easily and quickly obtained and was inherently biocompatible. The drawback of autologous blood clot is that as the body's natural clot dramatically limits the durability of occlusion; recanalization can recur within hours to days. Silk threads were also historically used as embolic agents, notably for intracranial vascular malformations. Metallic embolization coils have also been used to stop bleeding or abnormal blood flow within an artery. Even though coils have useful physico-mechanical properties such as inherent radiopacity and shape memory they have a number of disadvantages including inter alia, large size, poor distal access, chronic tissue damage, tissue hyperplasia, vessel occlusion and permanent incorporation into the tissue at the deployment site. Nonmetallic alternatives to embolization include liquid and particulate embolic agents.

Polymeric liquid embolic agents include precipitative and reactive systems. In a precipitative system a polymer dissolved in a biologically acceptable solvent that dissipate upon vascular delivery and allow the polymer to precipitate in the blood stream (U.S. Pat. No. 5,851,508). In the reactive systems monomeric cyanoacrylate mixture is introduced into the vascular site and polymerization takes place by the initiation of water in blood. The in situ polymerization of cyanoacrylate causes premature polymerization and adhesion to the delivery catheter. Precipitative compositions are easy to deliver and cause rapid embolization in the preferred site. In these compositions the polymer must be capable of rapid precipitation to form a cohesive mass upon contact with blood. The composition must be sterile, stable, biocompatible and highly radiopaque for the imaging techniques employed in radiology clinics.

Another advantage of liquid embolic system is that it can easily flow through the vessels and attain the required shape on precipitation. The biocompatible embolizing agent would produce a well-defined solid mass upon contact with blood and if any the X-ray contrast agent is present, it would permit visualization of the location of the embolism. A number of known radiopaque embolizing compositions are described in the prior art.

In one embodiment, a cellulose diacetate polymer, water miscible organic solvent, namely, dimethyl sulfoxide (DMSO) and a water insoluble contrast agent such as tantalum, tantalum oxide and barium sulfate are used as embolic composition (U.S. Pat. No. 5,580,568).

The U.S. Pat. No. 5,851,508 discloses a composition suitable for embolization which has an ethylene vinyl alcohol copolymer, water miscible organic solvent DMSO and a water insoluble contrast agent such as tantalum, tantalum oxide and barium sulfate.

Another composition described in U.S. Pat. No. 5,695,480 uses a biocompatible polymer selected from cellulose acetate, cellulose acetate propionate, cellulose acetate butyrates, ethylene vinyl alcohol copolymer, hydrogels, poly acrylonitrile, poly vinyl acetate, nitro cellulose, copolymers of urethane/carbonate, copolymers of styrene/maleic acid and a biocompatible solvent such as DMSO, ethanol and acetone and a contrast agent such as tantalum, tantalum oxide, tungsten and barium sulfate.

In all these formulations the radiopaque contrast agent is suspended in the polymer solution and form a heterogeneous mixture. So permanent radiopacity cannot be achieved and sedimentation of metallic particle creates many problems.

A commercially available liquid embolic system (Onyx Liquid Embolic System, Medtronic Irvine, CA, USA) has the composition ethylene vinyl alcohol copolymer, DMSO as diluent and micronized tantalum powder as the radio contrast agent. It has the disadvantage of early sedimentation of the tantalum metal powder and associated catheter blockage. The metallic tantalum powder creates arcing and excessive fume generation in vascular channels during surgical quartering. It also causes significant artifacts while doing the follow up CT and MRI scans which obscure the visibility of adjacent normal structures. It also requires shaking for 20 minutes using a dedicated agitator for the uniform dispersion of the tantalum powder within the polymer solution and to obtain a homogeneous solution. This 20 minutes pre shaking precludes its use in emergency situations. It is very expensive as well. These formulations require careful preparation before use.

In order to overcome these drawbacks some of the recent inventors focused on the preparation of intrinsically radiopaque polymers for liquid embolic compositions.

Mottu et al., (2002) synthesized iodine containing cellulose mixed with ethers for embolization of aneurysms and arteriovenous malformation. Novel radiopaque polyurethane dissolved in ethanol added with DMSO is investigated by Maurer et al., (2000) for hepatic artery embolization. But the polymer was biodegradable which is not suitable for this application. Another system reported by Dudeck et al. (2006) used 4-iodo benzyl ester of poly vinyl alcohol which also exhibits the problem of degradation. Kocer et al. (2016) reported a dimethyl sulfoxide based embolic agent. They grafted triiodophenol on to a copolymer of poly-lactide-co-glycolide and poly hydroxyl ethyl methacrylate. In a Chinese patent grafting of pentaiodo compound N-(2,6-diiodo-carboxyphenyl)-3,4,5-triiodo Benzamide (DCPTB) with polyvinyl alcohol has been reported. But only 35-40% iodine was grafted onto the polymer.

So a low cost, metal powder free, biologically stable liquid embolic system with good clinical handling characteristics is essential for the treatment of above clinical conditions is still lacking.

OBJECTS OF THE INVENTION

It is therefore an object of this invention is to propose a radiopaque liquid embolic composition and a process for the preparation thereof.

It is a further object of this invention to propose a radiopaque liquid embolic composition.

Another object of this invention is to propose a radiopaque liquid embolic composition, which is highly radiopaque, homogenous, nontoxic and non-hemolytic.

Yet another object of this invention is to propose a radiopaque liquid embolic composition, which is a readily precipitating liquid embolic system suitable for embolization procedures.

It is a still further object of this invention to a radiopaque liquid embolic composition which is low cost, metal powder free, biologically stable liquid embolic system with good clinical handling characteristics.

These and other objects and advantages of the invention will be apparent from the ensuing description when read in conjunction with the accompanying drawings.

BRIEF DESCRIPTION OF THE ACCOMPANYING DRAWINGS

Figure 2:
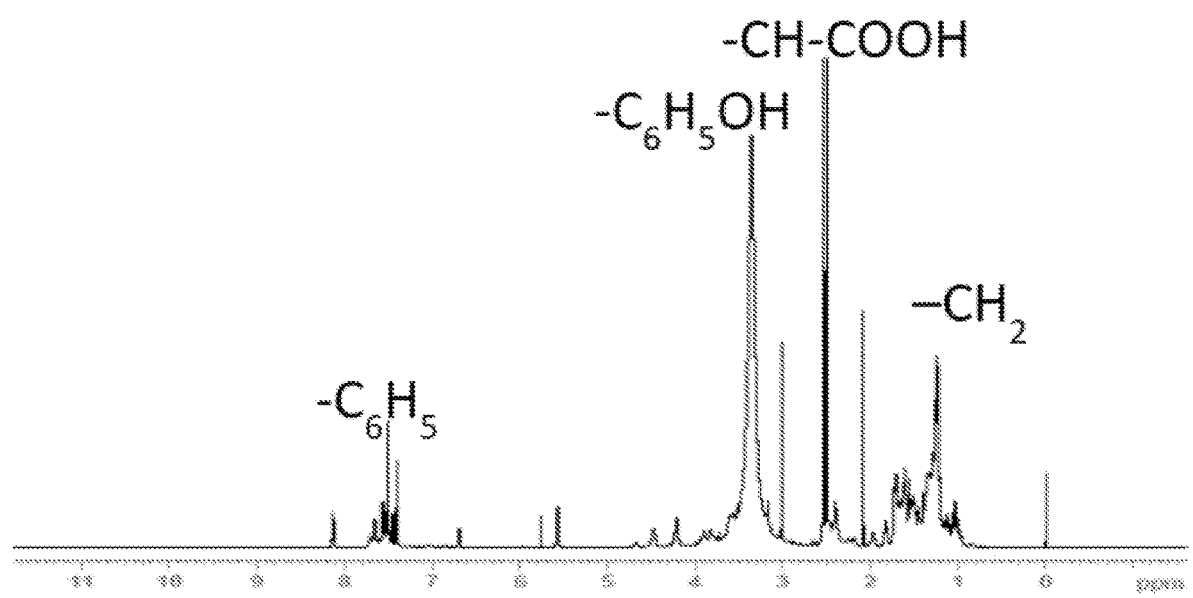
Figure 3:
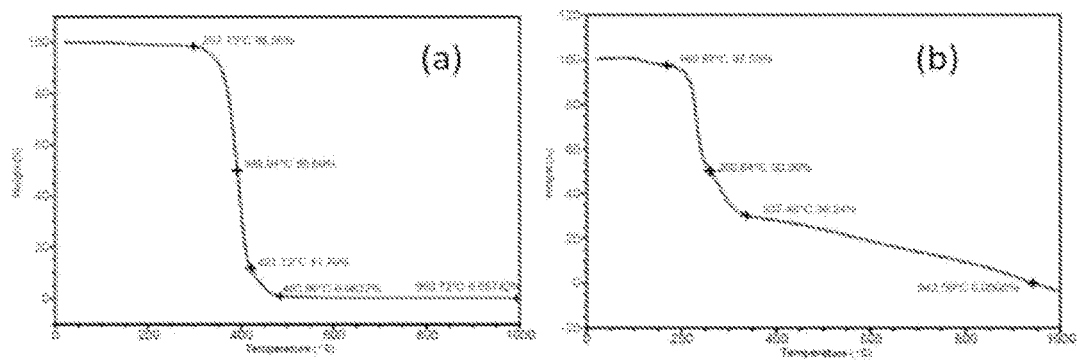
Figure 4:
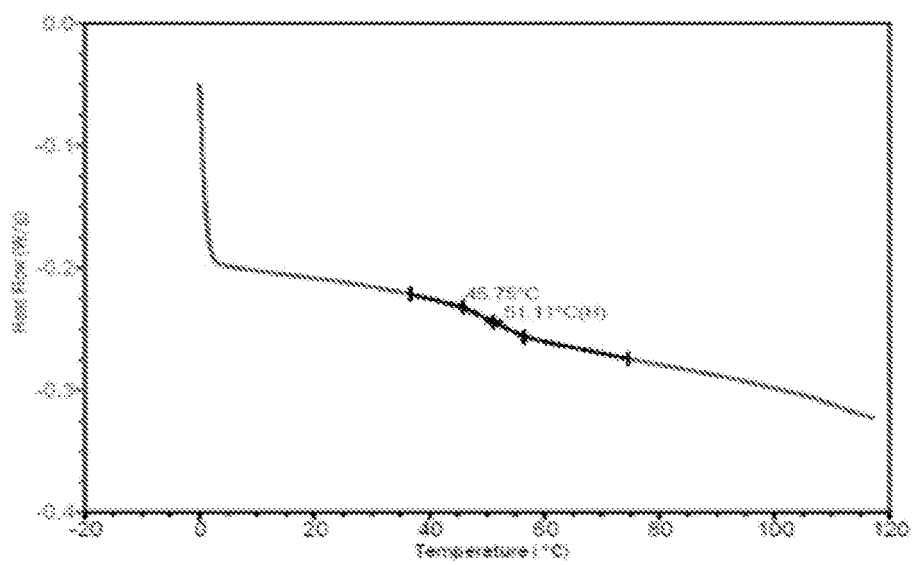
Figure 5:
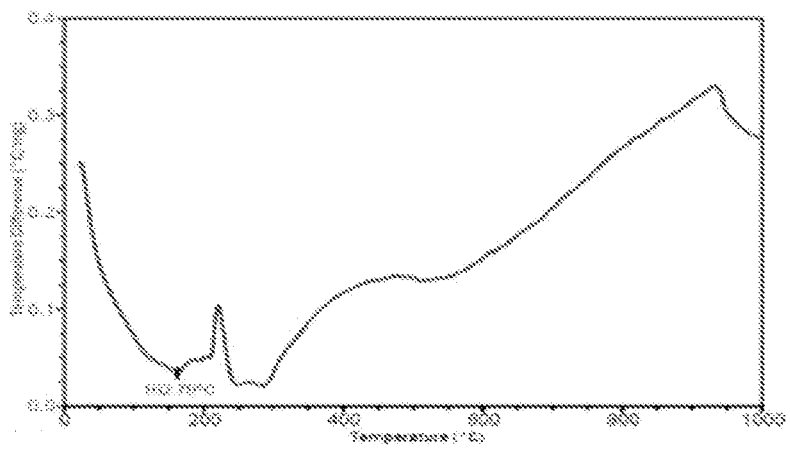
Figure 6:
Figure 7:
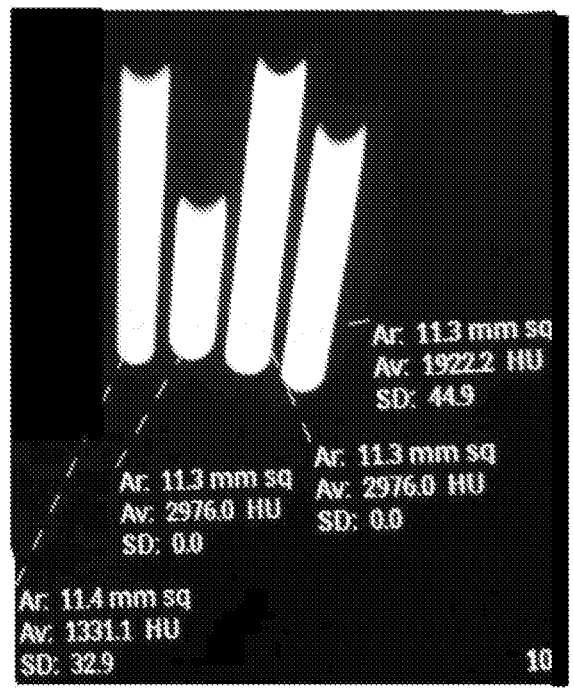

FIG. 1: Scheme of the grafting reaction
FIG. 2: $^1$H NMR of the grafted copolymer.

FIG. 3: Thermogravimetric analysis of the parent polymer, i.e., ethylene vinyl alcohol (EVOH) copolymer (FIG. 3 (*a*)) and grafted copolymer (FIG. 3(*b*)).

FIG. 4: Differential scanning calorimetry of the grafted copolymer.
FIG. 5: Differential thermal analysis of the grafted copolymer.
FIG. 6: Solution of Iodo compound grafted EVOH being injected into saline.
FIG. 7: Computerized X-ray images of IBHV-g-EVOH.

FIG. 8: Representative images showing the survival of cells after contacting with the 50% extract of IBHV-g-EVOH.

FIG. 9: MTT assay of L929 cells after contact with 50%, 25%, 12.5% and 6.25% extracts of test material.

BRIEF DESCRIPTION OF THE INVENTION

Thus according to this invention is provided a radiopaque liquid embolic composition and a process for the preparation thereof.

DETAILED DESCRIPTION OF THE INVENTION

According to this invention is provided a radiopaque liquid embolic composition and a process for the preparation thereof.

In accordance with this invention is provided a radiopaque, homogenous, non-adhesive, non-toxic polymeric material composition suitable for the embolization of blood vessels. As the first step an aromatic acid is iodinated to make it radiopaque and this iodo compound is reacted with ethylene vinyl alcohol copolymer (EVOH) to make the polymer radiopaque. The radiopaque polymer is dissolved in a water miscible organic liquid to convert it into a liquid embolic composition and this composition precipitates into a solid mass when it comes in contact with physiological fluids. The precipitated mass is non-cytotoxic, non-hemolytic and biologically stable. The embolic composition is suitable for blocking the blood vessels, aneurisms, supply vessels to tumors and arteriovenous malformations.

The injectable embolizing composition has a polymer content in the range of 10-45% (w/v) which helps to set different viscosity ranges for embolizing composition. The iodine content in the polymer is in the range of 30-70% (w/w) which helps to attain different opacity ranges for the embolizing composition. The embolic compositions can be modified to get viscosities in the range 5 centistokes to 500 centistokes.

The injectable embolizing composition can be used for embolizing blood vessels, tumor, aneurism and arterio-venous malformations.

Several variables control the efficacy of the solution as a liquid embolic agent

- Iodine content in the liquid embolic composition
- Vinyl alcohol content in the copolymer
- The ratio of polymer to iodocompound taken for synthesis
- Concentration of grafted polymer in the water miscible organic solvent
- Viscosity of the embolic system
- Sterilization technique used The grade of EVOH is defined by the mole % of ethylene content present in the copolymer. Several grades of EVOH are available (for example, 27 mol %, 32 mol & 38 mol %). The viscosity, solubility in the organic solvents, grafting reaction with the iodo compound, etc. depend on the ethylene content. Suitable solvents for the EVOH and the iodinated polymer are Dimethyl sulfoxide (DMSO) or N-methyl pyrrolidone (NMP).

First object of the present invention is the synthesis of tetra iodo compound, namely, 4,4-bis (4-hydroxy-3,5 diiodo phenyl)valeric acid of the chemical formula 1

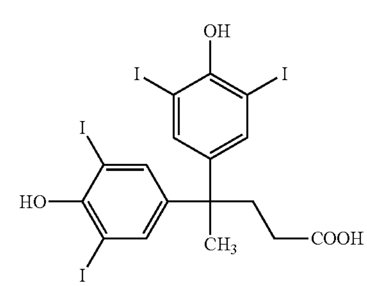

1

Synthesis of 4,4-bis (4-hydroxy-3,5 diiodophenyl) Valeric Acid (IBHV)

Iodination of 4,4-bis (4-hydroxyphenyl) valeric acid results the formation of 4,4-bis (4-hydroxy-3,5 diiodophenyl) valeric acid. The tetraiodocompound, 4,4-bis(4-hydroxy-3,5 diiodophenyl) valeric acid (IBHV) is synthesized by iodinating 4,4-bis (4-hydroxyphenyl) valeric acid (BHV). For this, BHV, an alkali and sodium iodide are dissolved in an alcohol. Sodium hypochlorite is added dropwise and stirred for 1 hr. An acid is added to precipitate the IBHV formed. This is washed and dried. The yield of the product obtained was 80%.

The reaction temperature has a strong influence on the iodination. The purity of the compound can be assessed by High Performance Liquid Chromatography. The compound can be characterized by FTIR spectroscopy, $^1$HNMR spectroscopy, Mass spectroscopy, Thermogravimetric analysis. Analysis: Molecular weight 789.69 g. In mass spectrum it is obtained as 812.69 (M+Na⁺ ion) & 834.67 (M+K⁺ ion). Thin layer chromatography (TLC) ethyl acetate/water (AcOEt/ H₂O: 3/8) R$_f$=0.46. For BHV, R$_f$=0.22

¹H NMR (DMSO) 9.48 (s, —COOH) 7.45 (s, —C₆H₅) 3.38 (s, —OH) 2.5 (triplet, CH—COOH) 1.4, 1.9, 2.1 ppm (multiplet, —CH₃).

The absence of aromatic proton peaks at 6.65 & 6.9 ppm in the ¹HNMR spectrum indicates the successful iodination of 4,4-bis (4-hydroxyphenyl) valeric acid.

Grafting of 4,4-bis (4-hydroxy-3,5 diiodophenyl) Valeric Acid onto EVOH

The grafting reaction can be carried out in the solution state. This is achieved by dissolving the EVOH and 4,4-bis (4-hydroxy-3,5 diiodophenyl) valeric acid in DMSO or NMP as illustrated in the scheme (FIG. 1). A suitable catalyst such as dimethyl amino pyridine is suitable for controlling the reaction. When the reaction conditions are favorable the iodo compound reacts with the EVOH polymer resulting the formation radiopaque polymer. When the reaction is complete the product may be purified by thorough washing with distilled water. The product may be obtained in the powder form by drying in an air oven. The grafted polymer can be characterized by FTIR spectroscopy, ¹HNMR spectroscopy, UV-Visible spectroscopy, Thermogravimetric analysis, Differential Scanning calorimetry & Differential thermal analysis. FTIR spectrum gives the ester C═O & C—O stretch at 1767 cm⁻¹ and 1116 cm⁻¹ respectively. Intensity of the —OH stretching vibration was found to decrease as the grafting progresses. In vitro cell culture cytotoxicity test using in L929 cells indicated that the compound was non-cytotoxic.

Radiopaque Liquid Embolic Composition

Radiopaque liquid embolic composition can be formulated by dissolving suitable concentrations of iodocompound grafted EVOH in DMSO or NMP. This composition is suitable for the occlusion of blood vessels, aneurysm and arteriovenous malformation by precipitation in the presence of blood or other physiological fluids. It is achieved by injecting the embolic composition at the required site with the aid of a catheter. The radiopacity of the system is measured by Computed Tomography (CT) scan. In a typical example, a solution of about 35% radiopaque polymer exhibits 2965 Hounsfield Units radiopacity which is adequate for imaging. Higher or lower Radiopacity can be achieved by manipulating the solution concentrations and/or iodine content in the composition. The viscosity of the composition can be adjusted by varying the concentration of the polymer in the solution or by changing the ethylene content of EVOH. The concentration of the polymer and the grade of EVOH affect the precipitation behavior of the system.

The tetraiodocompound, 4,4-bis(4-hydroxy-3,5 diiodophenyl) valeric acid (IBHV) was synthesized by iodinating 4,4-bis (4-hydroxyphenyl) valeric acid (BHV). For this, BHV, an alkali and sodium iodide were dissolved in an alcohol. Sodium hypochlorite was added dropwise and stirred for 1 hr. An acid is added to precipitate the IBHV formed. This is washed and dried. The yield of the product obtained was 80%.

Analysis: Molecular weight 789.69 g. In mass spectrum it is obtained as 812.69 (M+Na⁺ ion) & 834.67 (M+K⁺ ion). Thin layer chromatography (TLC) ethyl acetate/water (AcOEt/H₂O: 3/8) R$_f$=0.46. For BHV, R$_f$=0.22

¹H NMR (DMSO) 9.48 (s, —COOH) 7.45 (s, —C₆H₅) 3.38 (s, —OH) 2.5 (triplet, CH—COOH) 1.4, 1.9, 2.1 ppm (multiplet, —CH₃).

EVOH and IBHV are dissolved in dimethyl sulfoxide and 1,3-Dicyclohexylcarbodiimide and 4-Dimethylaminopyridine is added to this mixture and stirred for about 72 hrs. The reaction mixture is poured into water to precipitate the polymer. The precipitate is washed initially with water and later with methanol and finally dried in an air oven.

Analysis: ¹H NMR (DMSO) (FIG. 2) 2.5 ppm (proton adjacent to —COO group) 7.45 ppm (s, —C₆H₅) 3.35 ppm (phenolic proton) 1.4 ppm, 1.9 ppm, 2.1 ppm (methyl protons).

Thermal stability is analyzed by thermogravimetric analysis. The parent polymer, i.e., ethylene vinyl alcohol (EVOH) copolymer, was thermally stable upto 297° C. (FIG. 3 (a)) but grafting decreased the thermal stability to 169° C. (FIG. 3(b)).

The glass transition temperature of the grafted polymer is analyzed by differential scanning calorimetry. Its glass transition temperature (Tg) was found to be 51.1° C. (FIG. 4). EVOH had a Tg of 62° C.

From the differential thermal analysis traces showed that the melting point of IBHV-g-EVOH is 162.79° C. (FIG. 5). EVOH has a melting point of 172.23° C. Grafting decreases the melting point.

The iodo compound grafted EVOH is subjected to various tests for its physical and biological properties.

A solution of iodo compound grafted EVOH is dissolved in dimethyl sulfoxide. This solution is taken in a syringe and injected into saline. As the solution comes in contact with saline it forms into a solid mass.

The invention will now be explained in greater details with the help of the following non limiting examples. The examples are indicative of the invention but do not limit the scope of the claimed invention.

EXAMPLE

Example 1

The tetraiodocompound, 4,4-bis(4-hydroxy-3,5 diiodophenyl) valeric acid (IBHV) was synthesized by iodinating 4,4-bis (4-hydroxyphenyl) valeric acid (BHV). For this, 2 g BHV, 0.13 g sodium hydroxide and 6.3 g sodium iodide were dissolved in 50 mL methanol. Sodium hypochlorite (70 mL) was added dropwise and stirred for 1 hr. HCl (10% solution) was added to precipitate the IBHV formed. This was washed with distilled water and dried at 65° C. The yield of the product obtained was 80%.

Analysis: Molecular weight 789.69 g. In mass spectrum it was obtained as 812.69 (M+Na⁺ ion) & 834.67 (M+K⁺ ion). Thin layer chromatography (TLC) ethyl acetate/water (AcOEt/H₂O: 3/8) R$_f$=0.46. For BHV, R$_f$=0.22

¹H NMR (DMSO) 9.48 (s, —COOH) 7.45 (s, —C₆H₅) 3.38 (s, —OH) 2.5 (triplet, CH—COOH) 1.4, 1.9, 2.1 ppm (multiplet, —CH₃).

Example 2

EVOH (1 g) and IBHV (5 g) were dissolved in dimethyl sulfoxide (120 ml). Added 1,3-Dicyclohexylcarbodiimide (1.43 g) and 4-Dimethylaminopyridine (0.847 g) to this mixture and stirred for about 72 hrs. The reaction mixture was poured into water to precipitate the polymer. The precipitate was washed initially with water and later with methanol and finally dried in an air oven.

Analysis: $^1$H NMR (DMSO) (FIG. 2) 2.5 ppm (proton adjacent to —COO group) 7.45 ppm (s, —C$_6$H$_5$) 3.35 ppm (phenolic proton) 1.4 ppm, 1.9 ppm, 2.1 ppm (methyl protons).

Thermal stability was analyzed by thermogravimetric analysis. The parent polymer, i.e., ethylene vinyl alcohol (EVOH) copolymer, was thermally stable upto 297° C. (FIG. 3 (a)) but grafting decreased the thermal stability to 169° C. (FIG. 3(b)).

The glass transition temperature of the grafted polymer was analyzed by differential scanning calorimetry. Its glass transition temperature (Tg) was found to be 51.1° C. (FIG. 4). EVOH had a Tg of 62° C.

From the differential thermal analysis traces showed that the melting point of IBHV-g-EVOH was 162.79° C. (FIG. 5). EVOH has a melting point of 172.23° C. Grafting decreases the melting point.

Example 3

A solution (35%) of iodocompound grafted EVOH was dissolved in dimethyl sulfoxide. This was taken in a syringe and injected into saline. As the solution comes in contact with saline it formed into a solid mass (FIG. 6).

Example 4

Different solutions of grafted polymer (about 5 mL each) in DMSO were prepared and subjected to computerized X-ray imaging procedure in a computed tomography machine. In one composition, a 10% solution of IBHV-g-EVOH showed radiopacity of 1331 Hounsfield Units (HU). In another composition a 30% solution of IBHV-g-EVOH showed radiopacity of 2976 HU. In a third composition, a 35% solution of IBHV-g-EVOH showed 2976HU radiopacity. In yet another composition, a 15% solution of IBHV-g-EVOH showed radiopacity of 1922 HU (FIG. 7).

Example 5

Figure 8:
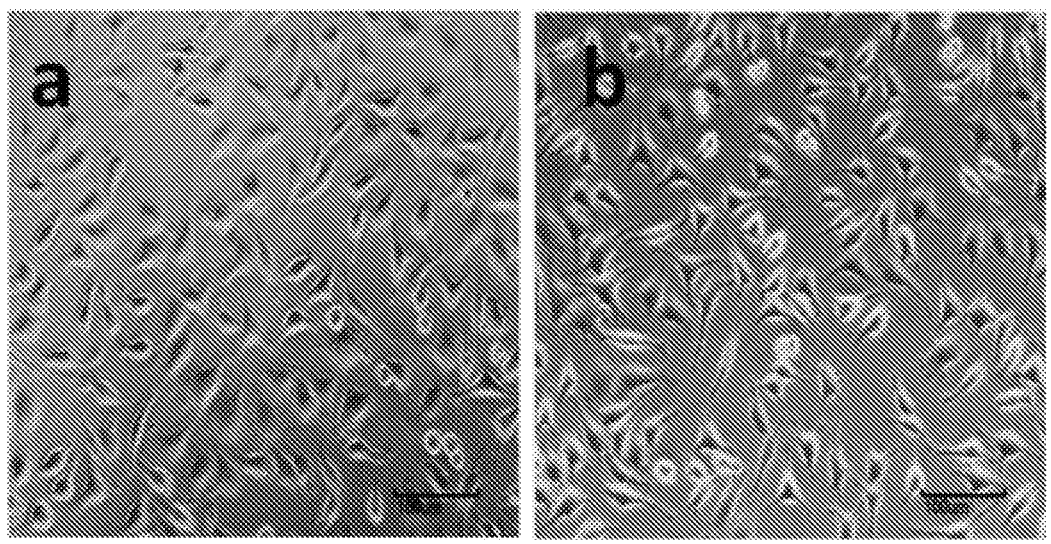
Figure 9:
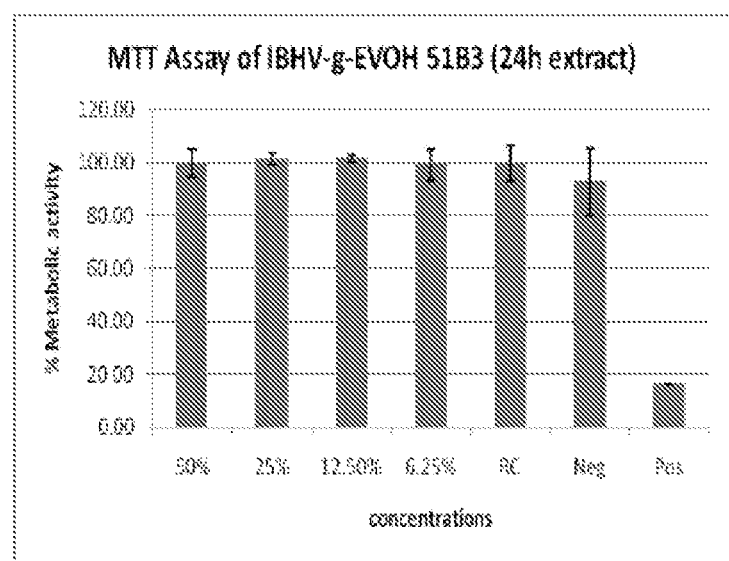

Biocompatibility evaluation of the grafted copolymers were carried out by performing in vitro cell culture cytotoxicity tests using L929 cell lines in accordance with ISO 10993-5 standard guidelines. For this purpose at first the grafted copolymer was sterilized by ethylene oxide. Extracts of the grafted copolymer was prepared by incubating 0.2 g of IBHV-g-EVOH in 1 mL physiological saline at 37±1° C. for 24±2 h at an extraction ratio of 1.25 cm$^2$/ml. Ultra high molecular weight polyethylene and dilute phenol were used as negative and positive controls, respectively. Results showed that extract of IBHV-g-EVOH did not cause any cytotoxic response. Representative images showing the survival of cells after contacting with the 50% extract of IBHV-g-EVOH is shown in the FIG. 8. The MTT assay of L929 cells after contact with 50%, 25%, 12.5% and 6.25% extracts of test material showed 99.66%, 101.34%, 101.51%, 99.20% metabolic activity, respectively (FIG. 9). It also revealed the non cytotoxic nature of the grafted copolymer. So from test on extract method and MU assay evaluation it is clear that the iodocompound grafted copolymer is non-cytotoxic.

Example 6

The sterile samples as described in example 5 were subjected to hemolysis test according to the procedure described in ISO 10993-4:2017 (Selection of tests for interaction of materials with blood). The percentage hemolysis in plasma samples after exposure to IBHV-g-EVOH was 0.02%. The result is the average of the experiment repeated at 3 times. According to ISO 10993-4: 2017, hemolysis rate less than 0.1% is considered non hemolytic.

Example 7

The solid mass obtained in example 3 was washed well with deionised water and lyophilized until it is free of water. The dried samples were weighed and placed in phosphate buffered saline in a shaking incubator at 37° C. and with an rpm of 80 for 3 months. The samples were washed with distilled water, lyophilized again to dry and weighed. None of the samples show any weight loss indicating that the samples are stable at these conditions.

The invention claimed is:

1. A radiopaque liquid embolic composition comprising tetra iodo compound, 4,4-bis (4-hydroxy-3,5 diiodo phenyl) valeric acid (IBHV), covalently linked to ethylene vinyl alcohol copolymer (EVOH) and dissolved in a water miscible organic liquid.

2. The radiopaque liquid embolic composition as claimed in claim 1, wherein said organic liquid is selected from Dimethyl sulfoxide (DMSO) or N-methyl pyrrolidone (NMP).

3. The radiopaque liquid embolic composition as claimed in claim 1, wherein the copolymer content is in the range of 10-45% (w/v) which helps to set different viscosity ranges for embolizing composition.

4. The radiopaque liquid embolic composition as claimed in claim 1, wherein the iodine content in the copolymer is in the range of 30-70% (w/w) which helps to attain different opacity ranges for the embolizing composition.

5. The radiopaque liquid embolic composition as claimed in claim 1, wherein the embolic composition can be modified to get viscosities in the range 5 centistokes to 500 centistokes.

6. The radiopaque liquid embolic composition as claimed in claim 1, wherein the embolic composition can be used for embolizing blood vessels, tumor, aneurism and arteriovenous malformations.

7. A process for the preparation of the liquid embolic composition as claimed in claim 1 comprising the steps of iodinating 4,4-bis (4-hydroxyphenyl) valeric acid (BHV) with sodium iodide followed by treatment with Sodium hypochlorite and an acid to obtain the tetraiodocompound, 4,4-bis(4-hydroxy-3,5 diiodophenyl valeric acid (IBHV), dissolving ethylene vinyl alcohol copolymer (EVOH) and IBHV in an organic solvent to form a mixture, adding 1,3-Dicyclohexylcarbodiimide and 4-Dimethylaminopyridine to this mixture and stirring followed by pouring the reaction mixture into water to precipitate the copolymer and dissolving the copolymer in an organic solvent to obtain the liquid embolic composition.

8. The process as claimed in claim 7, wherein said organic solvent is selected from Dimethyl sulfoxide (DMSO) and N-methyl pyrrolidone (NMP).

9. The process as claimed in claim 7, wherein the ethylene vinyl alcohol copolymer has ethylene content in the range 20 mol % to 50 mol % which is utilized for increasing the grafting efficiency of 4,4-bis (4-hydroxy-3,5 diiodo phenyl) valeric acid onto EVOH copolymer.

* * * * *